United States Patent
Brown et al.

(10) Patent No.: US 10,282,870 B2
(45) Date of Patent: May 7, 2019

(54) SPECTRAL IMAGING

(71) Applicant: KONINKLIJKE PHILIPS N.V., Eindhoven (NL)

(72) Inventors: Kevin Martin Brown, Chardon, OH (US); Reuven Levinson, Haifa (IL); Gilad Shechter, Haifa (IL); Mordechay Pinchas Freiman, Pardes Hanna (IL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 120 days.

(21) Appl. No.: 15/509,065

(22) PCT Filed: Oct. 10, 2015

(86) PCT No.: PCT/IB2015/057755
§ 371 (c)(1),
(2) Date: Mar. 6, 2017

(87) PCT Pub. No.: WO2016/059527
PCT Pub. Date: Apr. 21, 2016

(65) Prior Publication Data
US 2017/0278278 A1  Sep. 28, 2017

Related U.S. Application Data

(60) Provisional application No. 62/062,985, filed on Oct. 13, 2014.

(51) Int. Cl.
*G06K 9/00* (2006.01)
*G06T 11/00* (2006.01)
*G01N 23/046* (2018.01)

(52) U.S. Cl.
CPC .......... *G06T 11/003* (2013.01); *G01N 23/046* (2013.01); *G06T 11/005* (2013.01); *G06T 2211/408* (2013.01)

(58) Field of Classification Search
None
See application file for complete search history.

(56) References Cited

U.S. PATENT DOCUMENTS 4,789,930 A   12/1988  Sones
6,052,433 A    4/2000  Chao
(Continued)

OTHER PUBLICATIONS

Niu et al., "Iterative image-domain decomposition for dual-energy CT" 2014 Am. Assoc. Phys. Med., 2014, pp. 1-10. (Year: 2014).*
(Continued)

*Primary Examiner* — Wei Wen Yang

(57) ABSTRACT

A system includes memory (420) with instructions for at least one of processing spectral CT projection data to mitigate at least one of noise of the spectral CT projection data or a noise induced bias of the spectral CT projection data or generating a decomposition algorithm that mitigates the noise induced bias of the spectral CT projection data. The system further includes a processor (418) that executes the instructions and at least one of processes the spectral CT projection data or generates the decomposition algorithm and decomposes the spectral CT projection data to basis materials. The system further includes a reconstructor (434) that reconstructs the basis materials, thereby generating spectral images.

11 Claims, 9 Drawing Sheets

(56) References Cited

U.S. PATENT DOCUMENTS

| | | | |
|---|---|---|---|
| 6,678,350 B2 | 1/2004 | Dolazza | |
| 7,257,188 B2 | 8/2007 | Bjorkholm | |
| 8,199,874 B2 | 6/2012 | Toth | |
| 8,199,875 B2 | 6/2012 | Chandra | |
| 2012/0134561 A1 | 5/2012 | Xu | |
| 2014/0169520 A1* | 6/2014 | Langan | G01N 23/046 378/5 |
| 2014/0328465 A1* | 11/2014 | Herrmann | G01T 1/17 378/62 |
| 2015/0131883 A1* | 5/2015 | Taguchi | A61B 6/4241 382/131 |

OTHER PUBLICATIONS

Dobbins, et al., "Dose reduction in CT with correlated-polarity noise reduction: comparable image quality at half the dose with projection space processing", Proceedings of SPIE, vol. 8668, Mar. 6, 2013.

Dobbins, "Correlated polarity noise reduction for dual-energy imaging", Radiology, Radiological Society of North America 82nd Meeting, Dec. 1-6, 1996, abstracts., vol. 201 Suppl. 505.

Alvarez, et al., "Energy selective reconstructions in X-ray Computerized Tomography", Physics in medicine and biology, 21(5), 733-744, 1976.

Zhang, et al., "Objective characterization of GE Discovery CT750 HD scanner: Gemstone spectral imaging mode", Med. Phys. 38 (3), p. 1178, 2011.

Heismann, et al., "Quantitative image-based spectral reconstruction for computed tomography", Med. Phys. 36 (10), p. 4471, 2009.

\* cited by examiner

SPECTRAL IMAGING

CROSS REFERENCE TO RELATED APPLICATIONS

This application is the U.S. National Phase application under 35 U.S.C. § 371 of International Application No. PCT/IB2015/057755, filed Oct. 10, 2015, published as WO 2016/059527 on Apr. 21, 2016, which claims the benefit of U.S. Provisional Patent Application No. 62/062,985 filed Oct. 13, 2014. These applications are hereby incorporated by reference herein.

The following generally relates to spectral imaging and is described with particular application to computed tomography (CT).

Spectral (or multi-energy) CT utilizes multiple attenuation values acquired at multiple different photon energies to solve for photoelectric effect, Compton scatter, and other component(s) (e.g., one or more K-edge) contributions of the mass attenuation coefficient of a material. This allows for reconstruction of virtual monochromatic images, iodine concentration maps, virtual non-contrast images, etc., as well conventional CT images. There are several approaches for acquiring such attenuation values, including using multiple x-ray tubes, kVp switching, multi-layer detectors, and photon counting detectors.

With dual-energy CT, the literature has indicated that the energy-dependent attenuation of a material ($\mu_i(E)$) can be approximated as a linear combination of the attenuation profiles of the photoelectric effect ($C_i^P \mu_w^P(E)$) and Compton scatter ($C_i^s \mu_w^s(E)$) contributions in water as shown in EQUATION 1:

$$\mu_i(E) = C_i^P \mu_w^P(E) + C_i^s \mu_w^s(E). \quad \text{EQUATION 1:}$$

A set of images with pixel values that represent the coefficients $C^P$ and $C^s$ of the photoelectric effect and Compton scatter can be reconstructed from the corresponding line integrals ($l^P$ and $l^s$). The line integrals can be obtained from the two different energy spectra $F_H$ and $F_L$ (L=low energy and H=high energy) through EQUATION 2:

$$p_{H/L} = -\log\left(\frac{\int_0^\infty dE\, E \cdot F_{H/L}(E) \cdot \exp(-\mu_w^P(E) \cdot l^P - \mu_w^s(E) \cdot l^s)}{\int_0^\infty dE\, E \cdot F_{H/L}(E)}\right). \quad \text{EQUATION 2}$$

Here, the terms $F_{H/L}(E)$ are the flux of the high- and low-spectrum, obtained by modelling the flux emitted towards the detector pixel from the upper beam, and the detector response. The difference between the two spectra can result either due to tube modulation or due to two detector layers.

The terms $l^{p/s}$ are the photoelectric and scatter equivalent paths in water, and $\mu_w^{p/s}(E)$ are the energy dependent attenuation coefficients of these two mechanisms. $l^p$ and $l^s$ can be solved by inverting EQUATION 2, which amounts to a mapping function from the domain of $p_L$ and $p_H$ into the domain of the $p_s$ and $p_p$: $(p_s, p_p) = \mathcal{D}(p_L, p_H)$. Here, $p_s$ and $p_p$ are obtained from $l^{p/s}$ by multiplying them with fixed scalar attenuation coefficients in order to process later on dimensionless prep values for convenience. $\mathcal{D}()$ has been solved through a polynomial function or a look-up table.

Unfortunately, the decomposition function $\mathcal{D}()$ is non-linear. As such, in the presence of noisy data, the mean of the decomposition is not equal to the decomposition of the mean of the inputs, or $(\overline{P_s}, \overline{p_p}) \neq \mathcal{D}(\overline{p_{Li}}, \overline{P_{Hi}})$. As a consequence, the decomposition will include a bias. This noise induced bias varies within the sinogram and propagates to artificial bias in the reconstructed photo and scatter images. Furthermore, this leads to inaccurate iodine concentration estimations, as well as to visible image artifacts in virtual monochromatic images.

The low and high energy projections each have a statistical distribution resulting from the random nature of the X-ray photons (photon shot noise), which can be described within a good approximation by a Gaussian function, as a result of the photon Poisson behavior. Within a monochromatic approximation, and neglecting electronic noise, the projection values will have a normal distribution with a standard deviation ($\sigma$) equal to the inverse of the square root mean photon count value ($\mu$). The distribution of low and high energy projection pairs is not correlated and has random polarity, each polarity combination (+,+), (−,+), (−,−), and (+,−) being equal. From FIG. 1, the low and high energy projection pairs are evenly distributed over same polarity quadrants I and III and opposite polarity quadrants II and IV.

With dual energy CT, the decomposition algorithm generates two data sets, such as a photoelectric data set (PE) and a Compton scatter data set (Sc). Note that the PE/Sc decomposition can be considered equivalent to a basis material decomposition (i.e. water/iodine) to within an "angle" constant. The two data sets are produced in pairs: (low energy projections, High energy projections)$_{p,v}$ => (PE, Sc)$_{p,v}$ for each projection "p" and view "v". The decomposition creates a negative correlation between the photoelectric effect and Compton scatter data sets. The correlation factor is a function of the dual energy attenuation coefficients of the photoelectric and Compton scatter components. FIG. 2 shows PE, Sc pairs).

FIG. 3 shows the low and high energy projection data pairs 302, which have equal variation from a mean value 304, mapped to their values of Sc and PE 306 via a decomposition mapping 308. Unfortunately, the decomposition is sensitive to the relative polarity of the low and high energy projection data pairs, and the noise is amplified for low and high energy projection data pairs of opposite polarity. This can be seen in FIG. 3 by the large variations 310 and 312 in quadrants II and IV. Due to photon shot noise, the "opposite polarity" variation occurs approximately 50% of the time.

Aspects described herein address the above-referenced problems and others.

In one aspect, a system includes memory with instructions for at least one of processing spectral CT projection data to mitigate at least one of noise of the spectral CT projection data or a noise induced bias of the spectral CT projection data or generating a decomposition algorithm that mitigates the noise induced bias of the spectral CT projection data. The system further includes a processor that executes the instructions and at least one of processes the spectral CT projection data or generates the decomposition algorithm and decomposes the spectral CT projection data to basis materials. The system further includes a reconstructor that reconstructs the basis materials, thereby generating spectral images.

In another aspect, a method includes at least one of processing spectral CT projection data to reduce noise or noise induced bias or generating a decomposition that reduces the noise induced bias for the spectral CT projection data. The method further includes decomposing the spectral CT projection data to generate basis materials. The method further includes reconstructing the basis materials to generate spectral images.

In another aspect, a computer readable storage medium is encoded with computer readable instructions. The computer readable instructions, when executed by a processer, cause the processor to: at least one of processes dual-energy CT projection data or generate a decomposition algorithm for the dual-energy CT projection data; decompose the dual-energy spectral CT projection data to generate basis materials, and generate spectral images by reconstructing the basis materials.

The invention may take form in various components and arrangements of components, and in various steps and arrangements of steps. The drawings are only for purposes of illustrating the preferred embodiments and are not to be construed as limiting the invention.

Figure 4:
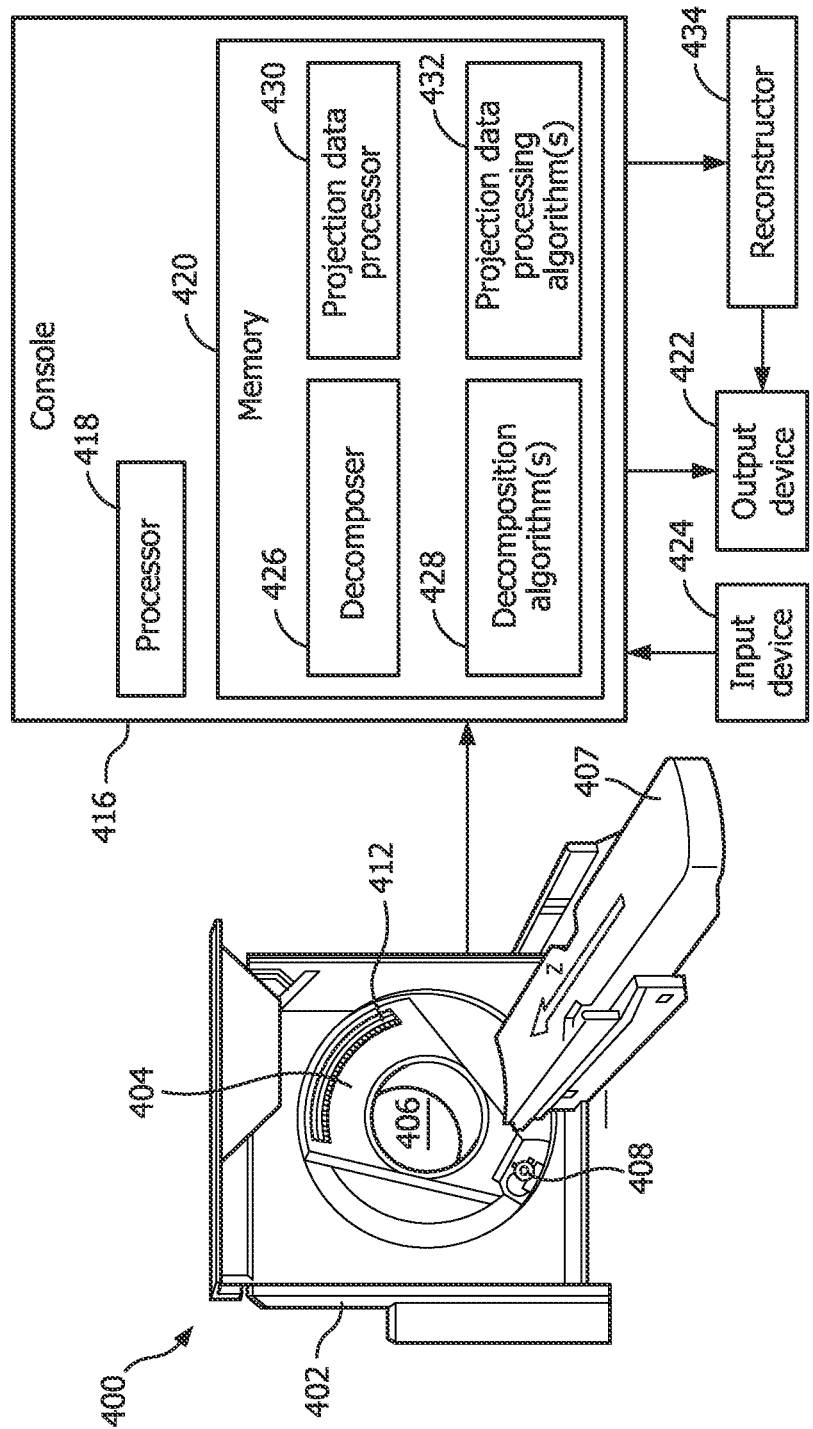

FIG. 4 schematically illustrates an example imaging system with a console with a material basis decomposer and a projection data processor.

Figure 5:
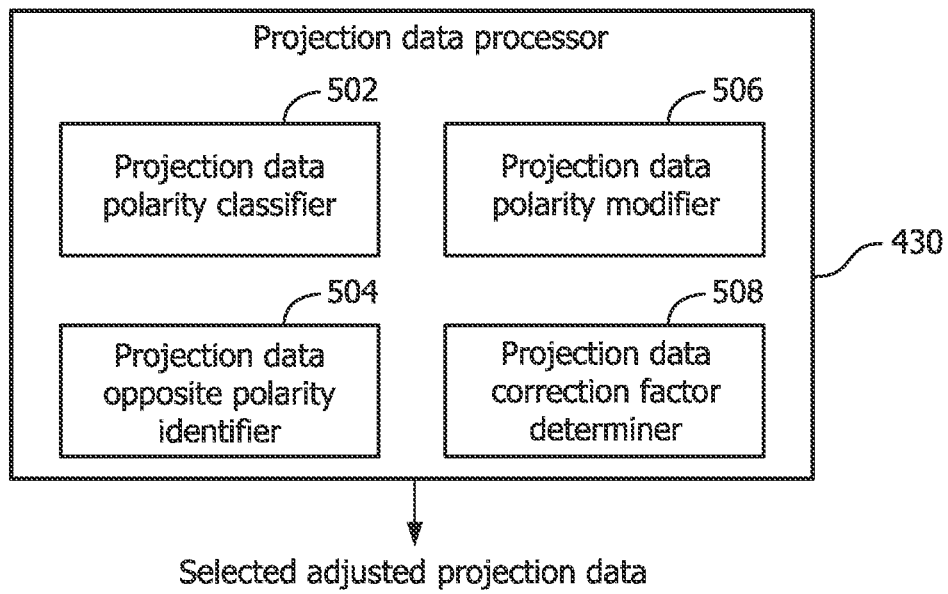

FIG. 5 schematically illustrates an example of the projection data processor.

Figure 6:
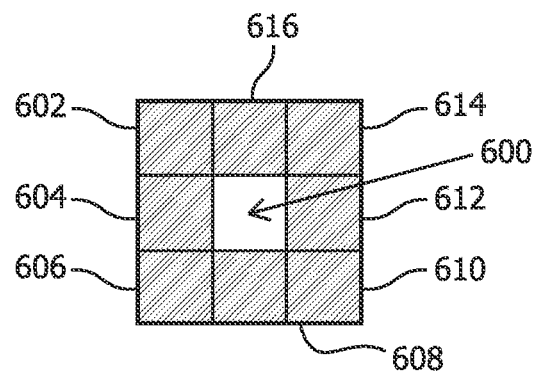

FIG. 6 shows an example of calculating the local mean values from a set of spatial neighbors.

Figure 7:
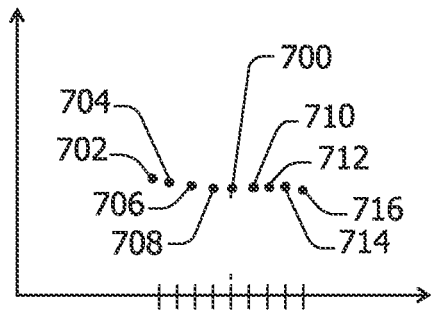

FIG. 7 shows an example of calculating the local mean values from a set of temporal neighbors.

Figure 8:
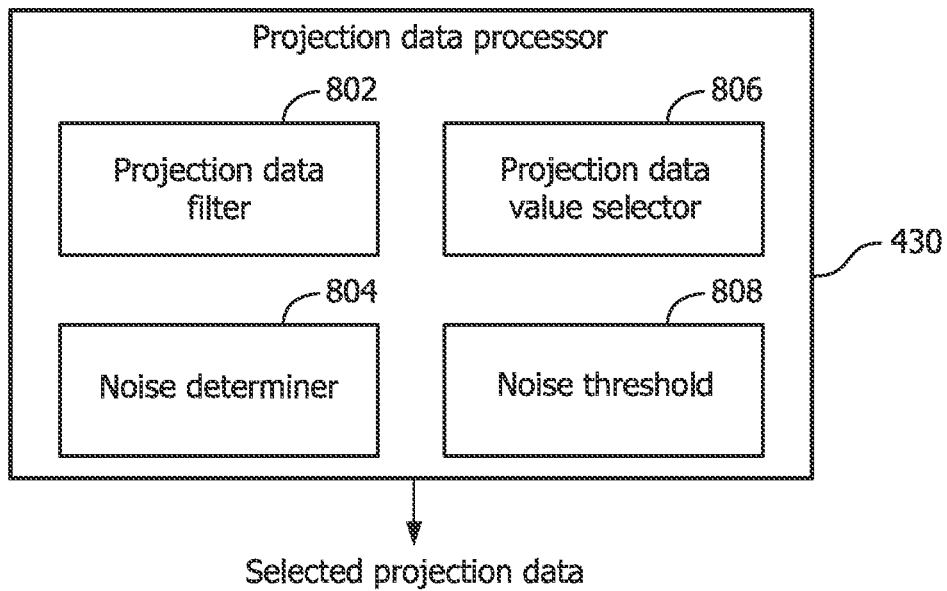

FIG. 8 schematically illustrates another example of the projection data processor.

Figure 9:
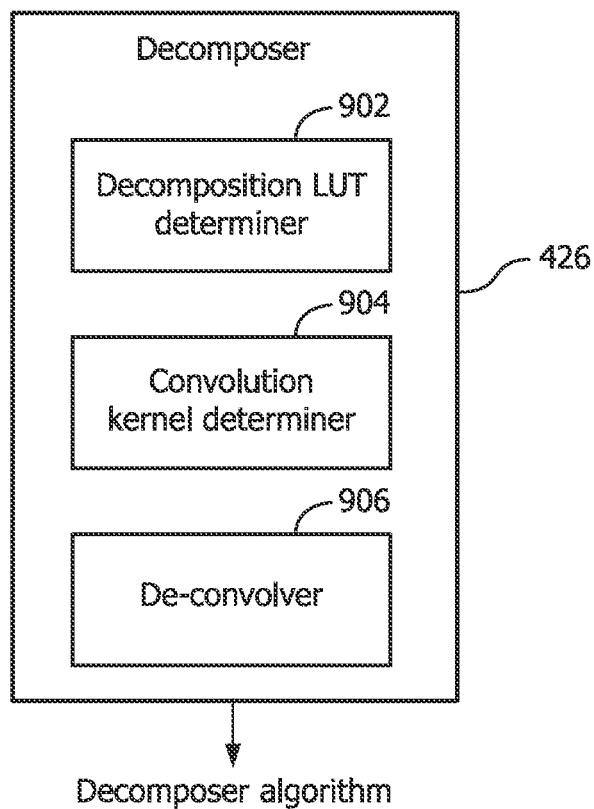

FIG. 9 shows the decomposition input range and the location of one of its columns.

Figure 10:
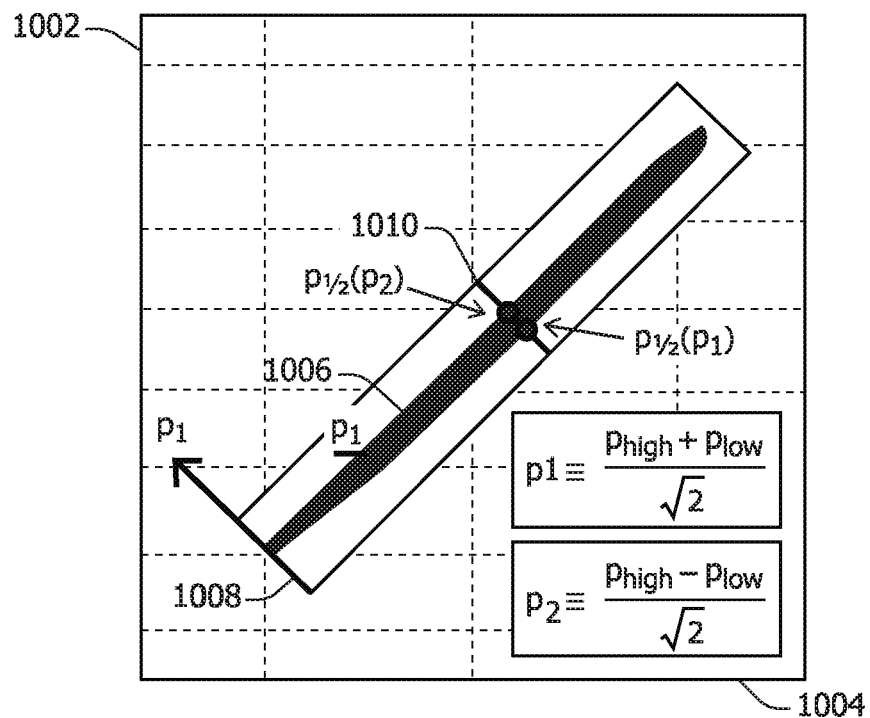

FIG. 10 shows a curve that represents a solution of a de-convolution along one of its columns.

Figure 11:
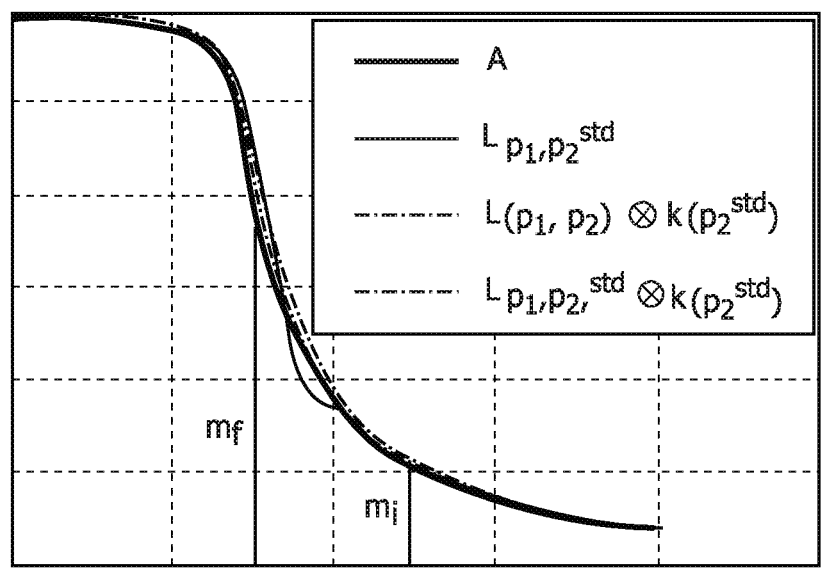

FIG. 11 shows a solution for the photoelectric effect LUT.

Figure 12:
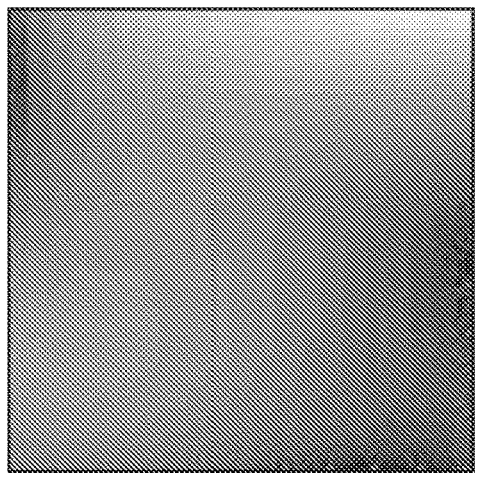

FIG. 12 shows example values for the photoelectric effect LUT.

Figure 13:
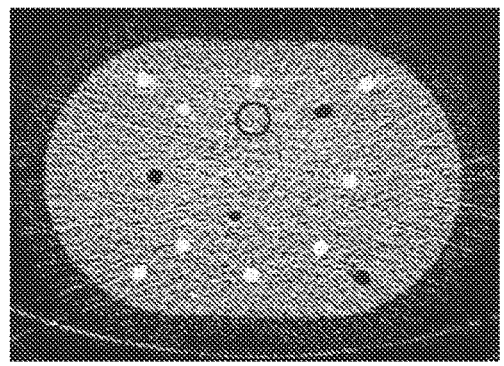

FIG. 13 shows a prior art approach using a decomposition algorithm that does not include de-biasing.

Figure 14:
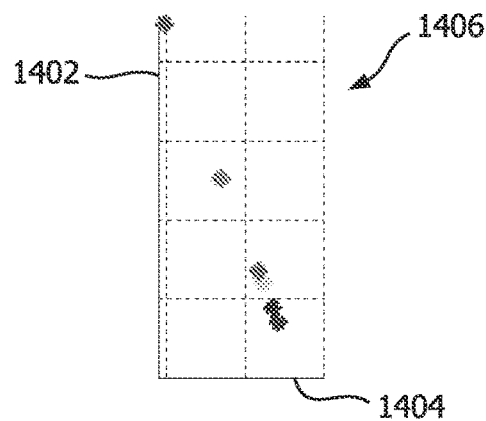

FIG. 14 shows a scatter plot corresponding to FIG. 13.

Figure 15:
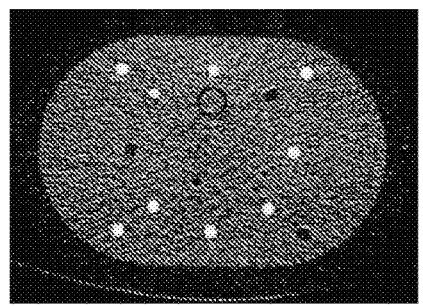

FIG. 15 show a photoelectric effect image using a decomposition algorithm discussed herein which includes de-biasing.

Figure 16:
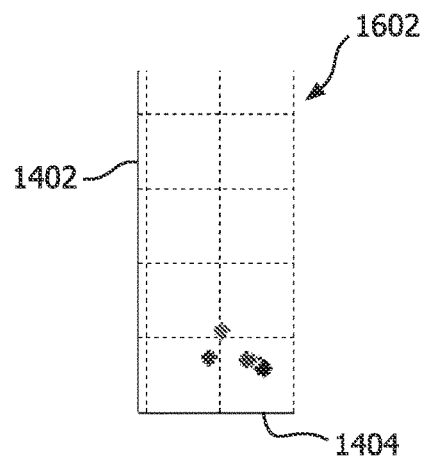

FIG. 16 shows a scatter plot corresponding to FIG. 15.

Figure 17:
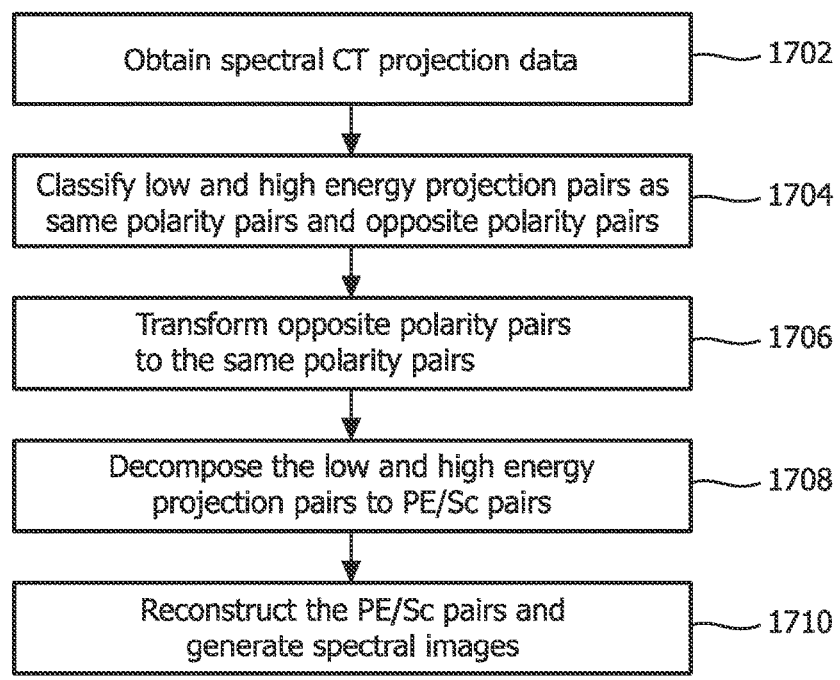
Figure 18:
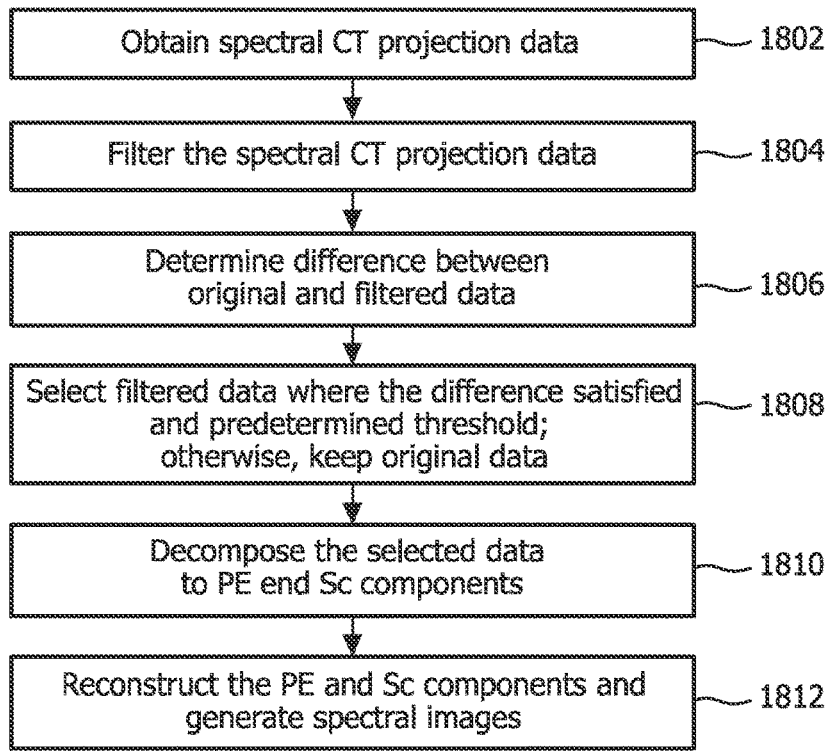
Figure 19:
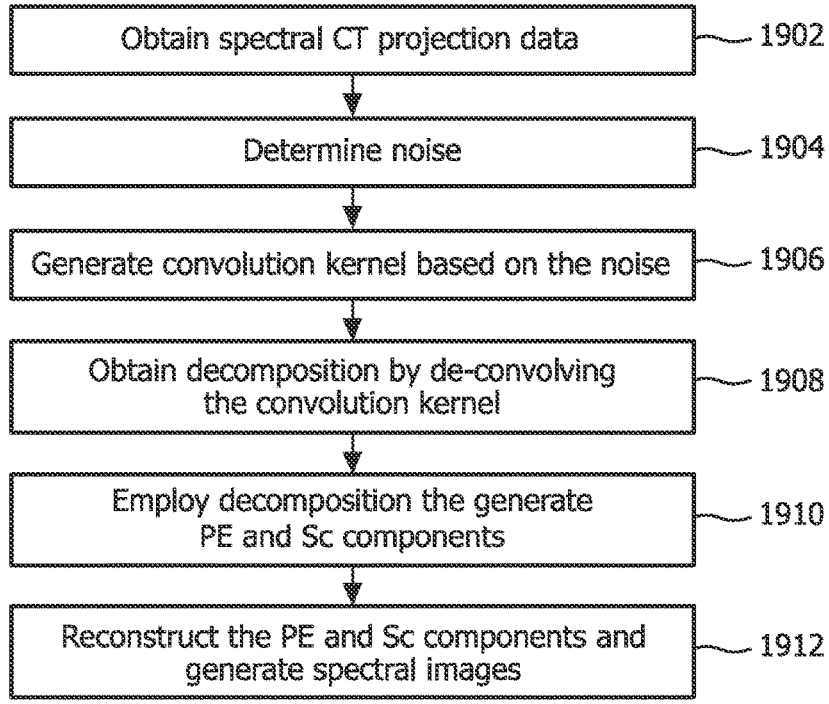

FIGS. 17, 18 and 19 illustrate example methods.

Initially referring to FIG. 4, an imaging system 400, such as a computed tomography (CT) scanner, is illustrated. The imaging system 400 includes a stationary gantry 402 and a rotating gantry 404, which is rotatably supported by the stationary gantry 402 and rotates around an examination region 406 about a z-axis. A subject support 407 such as a couch supports a subject or object in the examination region 406. The subject support 407 is movable in coordination with scanning so as to guide the subject or object with respect to the examination region 406 for scan of the subject or object.

A radiation source 408, such as an x-ray tube, is rotatably supported by the rotating gantry 404, rotates with the rotating gantry 404, and emits radiation that traverses the examination region 406. In one instance, a controller controls a mean or peak emission voltage of the radiation source 408. This includes switching the emission voltage between two or more emission voltages (e.g., 80 and 140 kVp, 100 and 120 kVp, etc.) within an integration period and/or otherwise. In a variation, the imaging system 400 includes at least two radiation sources 408 that emit radiation at different emission voltages. In another variation, the radiation source 408 includes a single broad spectrum x-ray tube.

A detector array 412 subtends an angular arc opposite the examination region 406 relative to the radiation source 408. The detector array 412 detects radiation that traverses the examination region 406 and generates projection data indicative thereof. Where the radiation source voltage is switched between at least two emission voltages and/or two or more x-ray tubes emit radiation at two different emission voltages, the detector array 412 generates projection data for each of the radiation source voltages. For a single broad spectrum x-ray tube, the detector array 412 includes an energy-resolving detector (e.g., multi-layered, photon counting, etc.) that produces spectral projection data.

A computing system serves an operator console 416 and includes at least one processor 418 (e.g., a microprocessor, a central processing unit, etc.) that executes at least one computer readable instruction stored in computer readable storage medium ("memory") 420, which excludes transitory medium and includes physical memory and/or other non-transitory medium. The microprocessor 418 may also execute one or more computer readable instructions carried by a carrier wave, a signal or other transitory medium. The computing system 416 further includes an output device(s) 422 such as a display monitor, a filmer, etc., and an input device(s) 424 such as a mouse, keyboard, etc.

In the illustrated example, the at least one computer readable instruction implements a decomposer 426, which decomposes spectral projection data based on a decomposition algorithm(s) 428, and a projection data processor 430, which processes spectral projection data based on a projection data processing algorithm(s) 432. As described in greater detail below, in one instance, the decomposer 426 decomposes the spectral projection data into basis materials, such as photoelectric and Compton scatter components and/or other basis materials, using a decomposition algorithm(s) 428 that reduces noise induced bias. Also described in greater detail below, in one instance, the projection data processor 430 processes the spectral projection data using a projection data processing algorithm(s) 432 that reduces noise induced bias and/or that reduces projection data noise.

The decomposition algorithm(s) 428 that reduces noise induced bias or another decomposition algorithm(s) 428 can be used with the processed spectral projection data. In a variation, one of more of the decomposer 426 or the projection data processor 430 is located in a computing apparatus separate and distinct from the console 416. Furthermore, in another variation, the projection data processor 430 is omitted. With this variation, the decomposition algorithm(s) 428 that reduces noise induced bias is utilized. The particular decomposition algorithm employed can be based on a default algorithm, an input indicative of a user selected algorithm of interest, the imaging protocol, etc. Likewise, the particular projection data processing algorithm employed can be based on a default algorithm, an input indicative of a user selected algorithm of interest, the imaging protocol, etc.

A reconstructor 434 reconstructs the decomposed spectral projection data. In one instance, the reconstructor 434 reconstructs one or more of the energy dependent basis materials, generating one or more images corresponding to one or more different energies. Additionally or alternatively, the reconstructor 434 combines the decomposed projection data and reconstructs non-spectral (or conventional) image data over the entire energy spectrum. In yet another instance, the one or more images corresponding to one or more different energies are combined to produce non-spectral (or conventional) image data. The decomposed spectral projection data can also be used to reconstruct virtual monochromatic images, iodine concentration maps, virtual non-contrast images, etc.

The illustrated console 416 processes spectral projection data obtained from the imaging system 400. In a variation, the spectral projection data is obtained from a different imaging system and/or a data repository such as a picture archiving and communication system (PACS), a radiology information system (RIS), a hospital information system (HIS), an electronic medical record (EMR), a database, a server, an imaging system, a computer and/or other data repository. The spectral projection data can be transferred via Digital Imaging and Communications in Medicine (DICOM), Health Level 7 (HL7), and/or other protocols.

FIG. 5 schematically illustrates an example of the projection data processor 430. The illustrated the projection data processor 430 includes a projection data polarity classifier 502, a projection data opposite polarity identifier 504, a projection data polarity modifier 506, and a correction factor determiner 508. For sake of brevity and clarity, the following is described in connection with dual energy projection data. However, it is to be appreciated that the projection data processor 430 can projection data for three or more different energy spectra.

Figure 1:
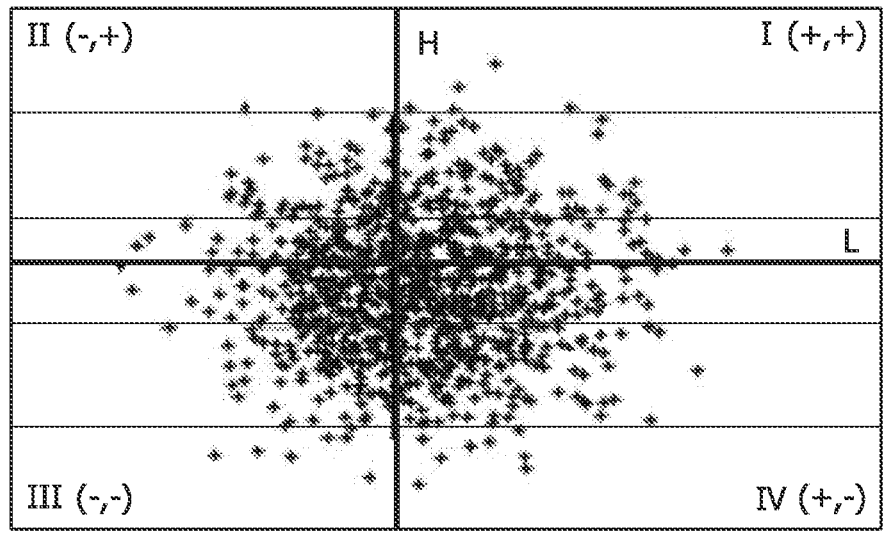
FIG. 1 shows low and high energy projection pairs evenly distributed in same polarity quadrants I and III and opposite polarity quadrants II and IV.
Figure 2:
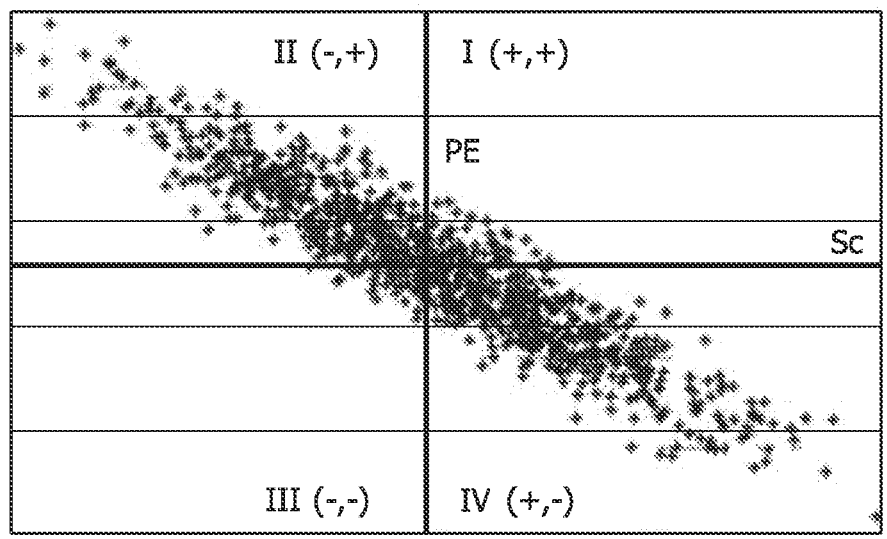
FIG. 2 shows photoelectric and Compton scatter component pairs.
Figure 3:
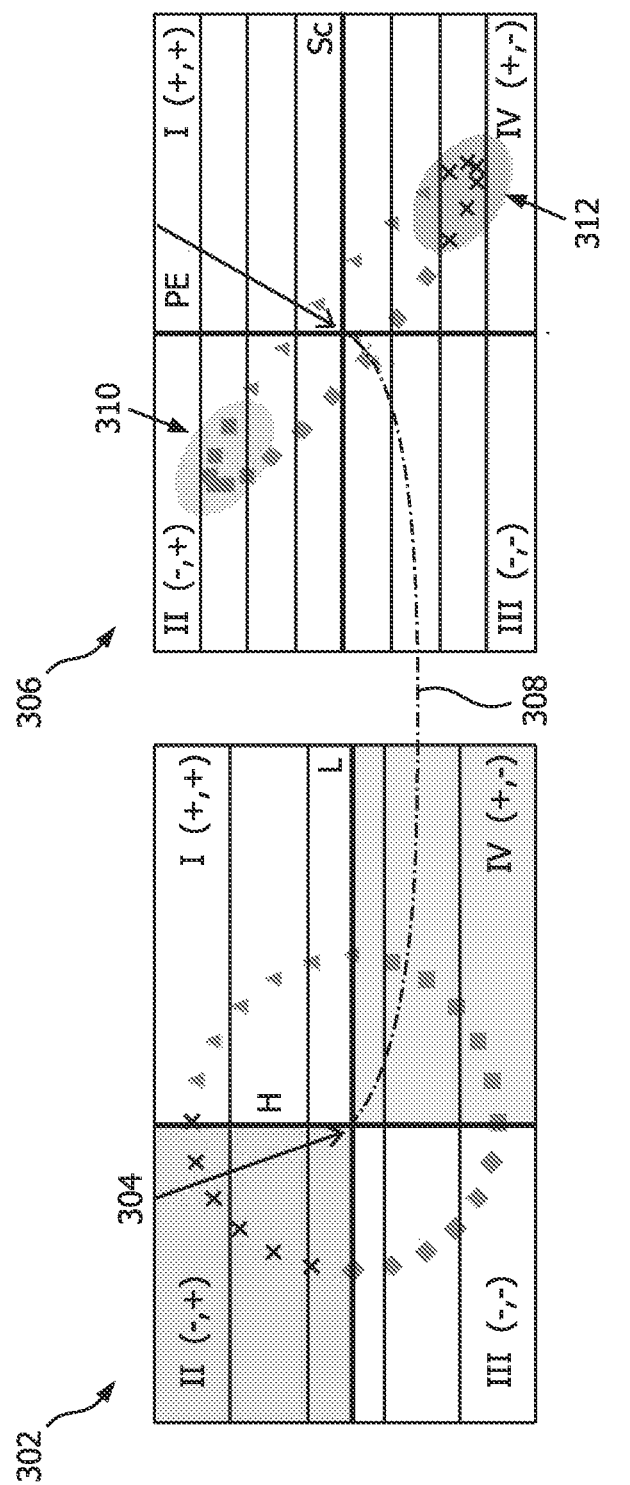
FIG. 3 shows the low and high energy projection data pairs, which have equal variation from the mean value, mapped to their values.

The projection data polarity classifier 502 classifies the low and high energy projection data pairs as either belonging to a same polarity quadrant (quadrant I and III in FIGS. 2 and 3) or an opposite polarity quadrant (quadrant II and IV in FIGS. 2 and 3). The classification can be done by comparing the measured low and high energy projection values to a local mean value of the low and high energy projection data. The local mean values can be calculated from a set of spatial neighbors and/or temporal neighbors.

FIG. 6 shows an example of calculating the local mean values from a set of spatial neighbors. In this example, a local mean value for pixel(n) 600 is determined as an average ($n_i$), where i=8, of the 8 spatial neighbors: $n_1$ (602), $n_2$ (604), $n_3$ (606), $n_4$ (608), $n_5$ (610), $n_6$ (612), $n_7$ (614), $n_8$ (616). FIG. 7 shows an example of calculating the local mean values from a set of temporal neighbors. In this example, a local mean value for pixel(n) 700 and view "j" is determined as an average ($v_j$), where j=−4, 4, of the 8 temporal neighbors: $v_{j-4}$ (702), $v_{j-3}$ (704), $v_{j-2}$ (706), $v_{j-1}$ (708), $v_{j+1}$ (710), $v_{j+2}$ (712), $v_{j+3}$ (714), $v_{j+4}$ (716). Other approaches are also contemplated herein.

Returning to FIG. 5, the local low and high energy projection mean values are not the true low and high energy projection data values. However, they are statistically closer to the true values than the individual low and high energy projection data values. The classification process does not have to have a 100% success rate. For Poisson statistical behavior (photon shot noise), a success rate based on 8-nearest spatial neighbors and 8-nearest temporal neighbors, for low frequency data, is above 90%.

A miss-classification occurs when a same polarity is calculated instead of opposite polarity or vice versa. For the former, no action is taken, the original projection data is used, and there is no reduction in the variation of the photoelectric and Compton scatter data pair. For the latter, the high energy projection data is incremented, the low and high energy projection data pair is now in the wrong quadrant, and there is an increase in the variation of the photoelectric and Compton scatter pair (or the photo-electric and Compton scatter surface density). A miss-classification occurs less than 10% of the time and causes a small decrease is the overall noise reduction.

The projection data opposite polarity identifier 504 identifies the low and high energy projection data pairs belonging to opposite polarity based on the classification. The projection data polarity modifier 506, for the low and high energy projection data pairs with the same polarity (quadrants I and III in FIG. 3), does not modify the low and high energy projection data pair polarity. However, for the low and high energy projection data pairs with opposite polarity (quadrants II and IV in FIG. 3), the polarity modifier 506 changes the polarity.

For example, if the high energy projection value is greater than a local mean value, which indicates the high energy projection value in opposite polarity quadrant II, the projection data polarity modifier 506 modifies the high energy projection value to be a high energy projection value in same polarity quadrant III. The projection data polarity modifier 506, in one instance, modifies the high energy projection value as shown in EQUATION 3:

$$\text{High\_Energy\_Projection\_Value} = \text{High\_Energy\_Projection} \quad \text{EQUATION 3:}$$

In another example, if the high energy projection value is less than the local mean value, which indicates the high energy projection value in opposite polarity quadrant IV, the projection data polarity modifier 506 modifies the high energy projection value to be a high energy projection value in same polarity quadrant I. The projection data polarity modifier 506, in one instance, modifies the high energy projection value as shown in EQUATION 4:

$$\text{High\_Energy\_Projection\_Value} = \text{High\_Energy\_Projection} \quad \text{EQUATION 4:}$$

The 2σ correction factor represents a "best guess". Due to the Poisson behavior, the variations the high energy projection value from the "true value" will be statistically distributed and the average variation is σ. The modification creates a low and high energy projection data pair with the same polarity variation. As such, to correct the polarity of the high energy projection value variation, twice the average variation value (2σ) is used. The 2σ correction value moves a low and high energy projection data pair with high energy projection value variation from 0 to 2σ from quadrant II to III. or quadrant IV to I.

The projection data correction factor determiner 508 determines the correction factor. In one non-limiting instance, the projection data correction factor determiner 508 determines the correction factor as shown in EQUATION 5:

$$2*\sigma = 2*\text{SQRT}[(\text{kV/mA factor})* ((\exp*\text{High\_Energy\_Projection})^{-1})] \quad \text{EQUATION 5:}$$

where the term "kV/mA factor" is an empirical value measured for each CT scanner, and, generally, is a measure of the X-ray tube flux (in air) at the detector surface.

The material basis decomposer 426 (FIG. 4) decomposes the polarity adjusted projection data. This projection data processor 430 does not require any change to the decomposition algorithm or other part of the processing chain.

FIG. 8 schematically illustrates another example of the projection data processor 430. In this example, the projection data processor 430 includes a projection data filter 802, a noise determiner 804, and a projection data value selector 806.

The projection data filter 802 filters the low and high energy projection data. Examples of suitable filters include, but are not limited to, a Gaussian filter (e.g., 3×3, etc.), an adaptive filter, a median filter, etc. Such filters smooth the low and high energy projection data.

The noise determiner 804 determines a noise value between the original projection data and the filtered projection data. This can be achieved by determining a difference between (e.g., by subtracting, adding the negative, etc.) the original projection data and the filtered projection data.

The projection data value selector 806 selects projection data to decompose based on the noise and a set of predetermined noise thresholds 808. Where the noise satisfies a predetermined noise threshold, the projection data value selector 806 selects the filtered projection. Otherwise, the projection data value selector 806 selects the original (or non-filtered) projection.

In one instance, different thresholds 808 are set for the low and the high energy projection data, and the filtered data is selected when the low energy projection data noise is positive and the high energy projection data noise is negative. In an absence of noise, the gradients on the signals $p_L$ and $p_H$ will nearly always be in the same direction. If under scanning conditions the low and high signals move in opposite directions, there is a high probability that this is due to noise, and not to real object features.

In another instance, the low value is set to the filtered low value only if the low signal error is greater than a first predetermined threshold and the high signal is less than a second predetermined threshold, and the high value is set to the filter high value only if the high signal error is less than a third threshold (which, in one instance, is the negative of the first threshold) and low signal error is greater than a fourth threshold (which, in one instance, is the negative of the second threshold).

In yet another instance, the low value is set to the filtered low value if the absolute value of a difference between the low error and the high error is greater than a predetermined threshold. Other selection criteria are also contemplated herein. The material basis decomposer 428 (FIG. 4) decomposes the selected projection data. This projection data processor 430 does not require any change to the decomposition algorithm or other part of the processing chain.

FIG. 9 illustrates an example in which the material basis decomposer 426 decomposes the spectral projection data using a decomposition algorithm(s) 428 that reduces noise induced bias. With this configuration, the projection data processor 430 and the projection data processing algorithm(s) 432 can be omitted. The material basis decomposer 426 includes a decomposition look-up table (LUT) generator 902, a convolution kernel determiner 904, and a de-convolver 906.

Generally, the decomposition algorithm(s) 428 mitigates the artificial bias in estimated photo and scatter equivalent paths. The decomposition function suitable for noiseless input spectral projection data replaced by spectral projection data that takes into account not only the low- and high-spectrum projections, but also the estimated noise of the their difference. In one instance, suppressing the bias is performed by solving the proper 1D de-convolution.

Briefly turning to FIG. 10, the input range of decomposition is shown. In FIG. 10, first and second axes 1002 and 1004 respectively represent high and low energy projection data. A region 1006 represents all practical pairs of low and high projection data values corresponding to the ray path emitted towards a given detector pixel. The region 1006 changes from one detector pixel to the other due to the variation of the spectra with the fan and the cone angles. A region 1008 represents pre-calculated look-up table (LUT) boundaries that are united for all detector pixels. The LUT input range is aligned to the axes $p_1$ and $p_2$. A line 1010 represents one specific LUT column.

With no noise correlation between the projections of the two spectra, $p_1$ and $p_2$ are uncorrelated and contain a similar noise level. Calculating the Eigenvectors and Eigenvalues of the discrete second derivative matrix applied on the LUT values suitable for noiseless input with respect to $p_1$ and $p_2$ shows that the LUT local non-linearity principal axis is very close to $p_2$. Therefore, only the noise component of $p_2$ is responsible for the noise induced bias we wish to avoid. The non-linearity along $p_2$ is expressing the loss of spectral separation for ray paths that intersect high atomic number materials. It becomes dominant at negative values of $p_2$ and high positive values of $p_1$.

Returning to FIG. 9, the decomposition LUT generator 902 generates a LUT from $\mathfrak{R}^3$ to $\mathfrak{R}$ for both scatter and photoelectric components. In addition to the conventional decomposition inputs i.e. the low and high energy projection values, the LUT takes, as an input, an estimated value for the noise standard deviation (STD) of $p_2$, denoted by $p_2^{STD}$. For each possible value of $p_2^{STD}$ the LUT is calculated column by column, i.e. by calculating it for all $p_2$ for each fixed value of $p_1$. A 1D function, denoted by $L_{p_1,p_2}^{STD}(p_2)$, is constructed that satisfies EQUATION 6:

$$2\overline{L_{p_1,p_2}^{STD}(p_1,s_2+n_2)} \approx L(p_1,s_2) \forall p_2^{f}(p_1) \leq s_2 \leq p_2^{1}(p_1). \quad \text{EQUATION 6:}$$

In EQUATION 6, $p_2$ is expressed as a sum of a noiseless signal component denoted by $s_2$ and a noise component denoted by $n_2$: $p_2=s_2+n_2$. The upper bar on the left hand side stands for a statistical expectation value of what is underneath. The variables $p_2^{f/l}$ on the right hand side are the intersections of the LUT column with the edges of the region 1006, as can be seen in FIG. 10. The function $L(p_1, s_2)$ on the right hand side contains the LUT column values suiting noiseless input values.

The last values are obtained by solving numerically the inverse relation to the one given as shown in EQUATION 2. The left hand side in EQUATION 7 can be written as a convolution between the noiseless solution $L(p_1, s)$ and a noise distribution kernel. Excluding the case of low signal at the detector and/or not applying any de-noising algorithm on the preps before de-composition, the convolution kernel determiner 904 may determine the convolution kernel $k(p_2^{STD})$ as a Gaussian within an approximation shown in EQUATION 7.

$$\overline{L_{p_1,s_2}^{STD}(p_1,s_2+n_2)}=L_{p_1,p_2}^{STD}(p_1,s_2) \otimes k(p_2^{STD}). \quad \text{EQUATION 7:}$$

Combining EQUATION 6 with EQUATION 7, $L_{p_1,p_2}^{STD}(p_2)$ can be expressed as a solution for the de-convolution shown in EQUATION 8, which is performed by the de-convolver 906:

$$L_{p_1,p_2}^{STD}(p_1,s_2) \otimes k(p_2^{STD})=L(p_1,s_2) \forall p_2^{f}(p_1) \leq s_2 \leq p_2^{i}(p_1). \quad \text{EQUATION 8:}$$

In order to avoid blown points, limit the global variation of $L_{p_1,p_2}^{STD}$ is limited with respect to $p_2$. In order not to increase the noise within the de-composed sinogram, a smooth and non-oscillating solution for $L_{p_1,p_2}^{STD}$ is obtained.

Following these guidelines, $L_{p_1,p_2}^{STD}$ is the minimizer of a quadratic three terms cost function shown in in EQUATION 9:

$$L_{p_1,p_2}^{STD} = \min_f(C(f));$$ EQUATION 9

$$C(f) = F(f) + S(f) + R(f);$$

Where $F(\theta)$ is a fidelity term, $S(\theta)$ is an auxiliary function of a limited output range, and $R(\theta)$ is a smoothness regularization term. Taking into account the discreteness of the sampling points of the decomposition LUT along $p_2$, these three terms can be expressed as shown in EQUATIONS 10, 11 and 12.

$$F(f) = \sum_{m=m_f}^{m_l}(h(m)-L(m))^2;$$ EQUATION 10

$$h = f \otimes k(p_2^{STD}),$$

$$S(f) = \beta_S \sum_{m=1}^{M}(f(m)-A(m))^2, \text{ and}$$ EQUATION 11

$$R(f) = \beta_R \cdot \sum_{m=1}^{M-1}(f(m+1)-f(m))^2,$$ EQUATION 12 where $m_f$ and $m_l$ are indices of the sampling points near $p_2^{fil}$, $\beta_S$ and $\beta_R$ are similarity and smoothness regularization parameters, M is a number of LUT points in one column, and A is an auxiliary function that equals to $L(p_1,s_2)$ between points $m_2^f$ and $m_2^l$ and is extrapolated out of this segment.

A solution for $L_{p_1,p_2}^{STD}$ as well as the noiseless case solution L, and the auxiliary function A are demonstrated in FIG. 11 for the photoelectric LUT. The derivatives of A at the LUT boundaries are intentionally about zero. This choice of extrapolation results in a solution for $L_{p_1,p_2}^{STD}$ that behaves similarly near the boundaries. This allows us to extrapolate $L_{p_1,p_2}^{STD}$ along $p_2$ out of the LUT in a smooth way by assigning for it constant values beyond the LUT boundaries for calculating the fidelity term $F(\theta)$. A can be prevented from exceeding a typical value of 10,000 at low values of $p_2$.

Convolving the noiseless solution for the LUT $L(p_1, s_2)$ with the noise kernel $k(p_2^{STD})$ shifts it from itself, see the black dashed curve. In contrast, convolving $L_{p_1,p_2}^{STD}$ with $k(p_2^{STD})$ results in the blue dashed curve that match pretty well the original profile of $L(p_1, s_2)$. This demonstrates the suppression of noise induced bias obtained. Due to the quadratic nature of the cost function $C(f)$, EQUATION 10 can be performed by a standard weighted standard least square fit. To improve the numerical stability, a conjugate gradient method can be used.

Example values of $\beta_R$ for the photoelectric LUT are shown in FIG. 12. The values of $\beta_S$ are chosen to be smaller than those of $\beta_R$ by about two orders of magnitude. LUT values are calculated EQUATION 10 for a discrete set of $p_2^{STD}$ values. An example for such a set can have a minimal value of 0.02 dimensionless natural prep units, an increment of 0.02, and a maximal value of 0.7. Taking $p_2^{STD}$ together with $p_1$ and $p_2$ obtained immediately from $p_{high}$ and $p_{low}$ as our three input parameters, a 3D LUT can be constructed for each detector pixel. However, to reduce calculation time and quota, 3D LUTs can be generated for a sub-set of the detector pixels contained in a 2D sub-set of the detector array. The plurality of these pre-calculated 3D LUTs can then be interpolated online for all the remaining detector pixels.

Left, however, for decomposing any given dual-energy sinogram by these LUTs is to calculate online an estimated sinogram for $p_2^{STD}$. Estimating this sinogram can be done based on the sinograms of $p_{high}$ and $p_{low}$ together with the known instantaneous tube current by noise propagation methods that incorporate the spectral model.

FIGS. 13 and 15 show a photoelectric effect images of solid water phantom containing Iodine, air and CaCl2 tubes, for a circular scan where the mAs=133. Window level/width are 50/−947 HU.

FIG. 13 is obtained from clipping the decomposition LUT along $p_2$ without de-biasing. The image suffers from streaks originating from blown points of photo equivalent path in water. The image also suffers from artificial whitening. FIG. 14 shows a corresponding scatter plot. In FIG. 14, a y-axis 1402 represents the photo-electric effect (in HU units), an x-axis 1404 represents the Compton-scatter (in HU units), and points 1406 represent mAs.

FIG. 15 is obtained utilizing the decomposition approach discussed herein and lacks the artifacts of FIG. 13. The average HU within the region of interest encircled by the purple circle equals to −942 for (a) and −955 (b). The rod of 570 mg/cc CaCl2 is encircled by a dashed yellow circle. FIG. 16 shows a corresponding scatter plot. In FIG. 16, the y-axis 1402 represents the photo-electric effect (in HU units), the x-axis 1404 represents the Compton-scatter (in HU units), and points 1602 represent mAs. The scatter plots of FIGS. 14 and 16 show how the approach described herein can suppress the mAs dependent noise induced HU bias within this rod.

FIG. 17 illustrates an example method for reducing spectral projection data noise in photoelectric and Compton scatter components.

It is to be appreciated that the ordering of the acts is not limiting. As such, other orderings are contemplated herein. In addition, one or more acts may be omitted and/or one or more additional acts may be included.

At 1702, spectral CT projection data is obtained. The spectral projection data includes at least two different energy spectra.

At 1704, the spectral projection data is classified into low and high energy projection pairs over same polarity and opposite polarity quadrants.

At 1706, the opposite polarity pairs are transformed to same polarity pairs.

At 1708, the adjusted projection data is decomposed to photoelectric and Compton scatter components.

At 1710, the photoelectric and Compton scatter components are reconstructed, producing spectral images.

FIG. 18 illustrates an example method for simulating a reduced contrast agent image in the projection domain.

It is to be appreciated that the ordering of the acts is not limiting. As such, other orderings are contemplated herein. In addition, one or more acts may be omitted and/or one or more additional acts may be included.

At 1802, spectral CT projection data is obtained. The spectral projection data includes at least two different energy spectra.

At 1804, the spectral projection data is smoothed by applying a smoothing filter to the data.

At 1806, differences between the original and the smoothed data are determined.

At 1808, the filtered data is selected where the difference satisfies a predetermined threshold and the original data is selected otherwise.

At 1810, the selected projection data is decomposed to photoelectric and Compton scatter components.

At 1812, the photoelectric and Compton scatter componentsare reconstructed, producing spectral images.

FIG. 19 illustrates an example method for simulating a reduced contrast agent image in the projection domain.

It is to be appreciated that the ordering of the acts is not limiting. As such, other orderings are contemplated herein. In addition, one or more acts may be omitted and/or one or more additional acts may be included.

At 1902, spectral CT projection data is obtained. The spectral projection data includes at least two different energy spectra.

At 1904, the noise of the spectral projection data is estimated.

At 1906, a convolution kernel is generated based on the noise.

At 1908, a decomposition is determined by de-convolving the convolution kernel.

At 1910, the decomposition is used to decompose the spectral projection data and generate photoelectric and Compton scatter components.

At 1912, the photoelectric and Compton scatter componentsare reconstructed, producing spectral images.

The method herein may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

It is to be understood that the embodiments described herein apply to basis materials such as photoelectric and Compton scatter components and/or other basis material pairs.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system, comprising:
memory, including instructions for processing spectral CT projection data;
a processor configured to execute the instructions and decompose the spectral CT projection data to basis materials;
a reconstructor configured to reconstruct the basis materials, thereby generating spectral images,
wherein the instructions include:
classifying low and high energy projection data pairs of the spectral CT projection data as same polarity pairs or opposite polarity pairs;
transforming the opposite polarity pairs to same polarity pairs to create modified spectral CT projection data; and
decomposing the modified spectral CT projection data to generate the basis materials.

2. The system of claim 1, wherein the processor is configured to classify the low and high energy pairs by comparing values of the low and high energy pairs with a local mean of the low and high energy pairs.

3. The system of claim 2, wherein the processor is configured to determine the local mean based on at least one of a predetermined spatial neighborhood or a predetermined temporal neighborhood about a low and high energy pair of interest.

4. The system of claim 2, wherein the processor is configured to transform an opposite polarity pair to same polarity pair by subtracting two times a standard deviation of a high energy value from the high energy value in response to the high energy value being greater than the local mean.

5. The system of claim 2, wherein the processor is configured to transform an opposite polarity pair to same polarity pair by adding two times a standard deviation of a high energy value to the high energy value in response to the high energy value being less than the local mean.

6. A method, comprising:
processing spectral CT projection data;
decomposing the spectral CT projection data to generate basis materials; and
reconstructing the basis materials to generate spectral images,
wherein the spectral CT projection includes low and high energy spectral projection data, and
wherein the processing of the spectral CT projection data includes:
filtering the low and high energy spectral projection data;
determining a difference between the original the low and high energy spectral projection data and the filtered the low and high energy spectral projection data;
comparing the difference to a set of predetermined noise thresholds;
selecting the filtered the low and high energy spectral projection data in response to the difference satisfying a predetermined noise threshold;
selecting the original the low and high energy spectral projection data in response to the difference not satisfying the predetermined noise threshold thereby creating selected spectral CT projection data; and
decomposing the selected spectral CT projection data to generate the basis materials.

7. The method of claim 6, wherein the filter is selected from a group consisting of a Gaussian filter, an adaptive filter, or a median filter.

8. The method of claim 6, wherein the filter is configured to smooth the low and high energy spectral projection data.

9. The method of claim 6, wherein the processing of the spectral CT projection data further includes:
selecting the filtered spectral projection data when a difference between the low original spectral projection data and the filtered low spectral projection data is positive or an absolute value of a difference between a low signal error and a high signal error is greater than a predetermine threshold.

10. The method of claim 6, wherein the processing of the spectral CT projection data further includes:
selecting the non-filtered spectral CT projection data when a difference between the high original projection data and the filtered high projection data is negative.

11. A computer readable storage medium encoded with computer readable instructions, which, when executed by a processor, causes the processor to:
process dual-energy CT projection data, wherein the processing of the dual-energy CT projection data includes:
determining a convolution kernel based on an estimated noise of the spectral CT projection; and
de-convoling the kernel to determine a decomposition function for the noise of the spectral CT projection, wherein the de-convoling includes minimizing a proper cost function;

decompose the dual-energy spectral CT projection data with the decomposition function to generate basis materials; and generate spectral images by reconstructing the basis materials.

* * * * *